United States Patent [19]

Andress, Jr.

[11] 4,097,389

[45] Jun. 27, 1978

[54] NOVEL AMINO ALCOHOL REACTION PRODUCTS AND COMPOSITIONS CONTAINING THE SAME

[75] Inventor: Harry J. Andress, Jr., Wenonah, N.J.

[73] Assignee: Mobil Oil Corporation, New York, N.Y.

[21] Appl. No.: 706,411

[22] Filed: Jul. 19, 1976

Related U.S. Application Data

[63] Continuation-in-part of Ser. No. 494,789, Aug. 5, 1974, abandoned.

[51] Int. Cl.$^2$ ............................................. C10M 1/32
[52] U.S. Cl. ................................... 252/51.5 A; 44/63; 252/32.5; 252/49.6; 252/49.9; 260/307 F
[58] Field of Search ................ 252/32.5, 49.6, 49.9, 252/51.5 A, 51.5 R; 260/307 F; 44/63

[56] References Cited

U.S. PATENT DOCUMENTS

| 3,087,936 | 4/1963 | LeSuer | 252/49.6 X |
| 3,160,634 | 12/1964 | Hodge | 252/51.5 R X |
| 3,219,666 | 11/1965 | Norman et al. | 252/51.5 A X |
| 3,306,908 | 2/1967 | LeSuer | 252/49.6 X |
| 3,369,021 | 2/1968 | LeSuer | 252/51.5 A X |
| 3,388,191 | 6/1968 | Cyba | 252/32.5 X |
| 3,446,808 | 5/1969 | Cyba | 252/49.6 X |
| 3,458,530 | 7/1969 | Siegel et al. | 252/51.5 A X |
| 3,502,677 | 3/1970 | LeSuer | 252/32.5 X |
| 3,920,567 | 11/1975 | Miller | 252/32.5 |

FOREIGN PATENT DOCUMENTS 1,444,904  2/1969  Germany ..................... 252/51.5 A Primary Examiner—Delbert E. Gantz
Assistant Examiner—Andrew H. Metz
Attorney, Agent, or Firm—Charles A. Huggett; Raymond W. Barclay; Claude E. Setliff

[57] ABSTRACT

Alkenylsuccinic anhydride is reacted with an amino alcohol, such as tris(hydroxymethyl)aminomethane, to provide intermediate reaction products from which novel derivatives are obtained by reacting the said intermediate product with boric acid or organoborates, organophosphonates and aldehydes. The intermediate reaction product prepared from tris(hydroxymethyl)aminomethane contains unexpectedly an oxazoline component when the reaction is carried out at 175° C or below, preferably 100° to 175° C. The reaction products and their derivatives are particularly useful in lubricants, fuels or other industrial fluids as detergents.

12 Claims, No Drawings

NOVEL AMINO ALCOHOL REACTION PRODUCTS AND COMPOSITIONS CONTAINING THE SAME

CROSS REFERENCE TO RELATED APPLICATIONS

This application is a continuation-in-part of U.S. application Ser. No. 494,789, filed Aug. 5, 1974, and was abandoned.

BACKGROUND OF THE INVENTION (1) Field of the Invention

This invention relates to novel nitrogen containing products and their use as detergents. In particular, this invention relates to amino alcohol reaction products.

(2) Prior Art of the Invention

British Patent Number 984,409 discloses the reaction, preferably at 180° to 250° C, between an alkenylsuccinic anhydride and an amine containing at least one hydroxyl group, such as tris(hydroxymethyl)aminomethane. The patent states that amide, imide or ester may be formed. These products are useful as lubricant additives. British Pat. No. 1,031,130 describes the reaction between a polyolefinic polysuccinic acid anhydride or halide and a hydroxylated amine such as tris(hydroxymethyl)aminomethane (hereinafter referred to as "TMAM"). These products are described as lubricant detergents.

U.S. Pat. No. 3,632,511 describes a two step process involving reaction between an olefin-substituted succinic acylating agent and an alkylene polyamine followed by the reaction mixture with a hydroxylamine, such as TMAM. U.S. Pat. No. 3,576,743 discloses the reaction between the alkenylsuccinic anhydride and a polyhydric alcohol followed by reaction of the resulting reaction product with a hydroxyl amine such as TMAM. In these two U.S. patents the resulting product is considered to be a mixture of different products. The products are said to have dispersant and rust resistant properties for lubricants and fuels.

U.S. Pat. Nos. 3,087,936; 3,284,409; 3,281,428 describe boron-containing additives; U.S. Pat. No. 3,280,034 describes aldehyde derivatives.

None of these above patents discloses the heterocyclic reaction products of the present invention or their derivatives.

SUMMARY OF THE INVENTION

It has now been discovered that the product of the reaction between an alkenylsuccinic acylating compound, namely anhydride or acid or acyl halide, with a hydroxyl primary amine may be further reacted with boric acid or an organoborate, organophosphonate or aldehyde to produce novel derivatives which provide detergent properties for lubricating oils and fuels.

DESCRIPTION OF SPECIFIC EMBODIMENTS

The alkenylsuccinic anhydrides used in this invention are normally prepared by reacting an olefin, preferably an olefin having from 8 to about 300 carbon atoms, with maleic anhydride. The preparation of these anhydrides is a known procedure. The anhydrides may also be prepared from chlorinated olefins with maleic anhydride to produce the corresponding alkenylsuccinic anhydride. Another method of preparing these anhydrides is by the catalytic method in which the olefin and maleic anhydride are mixed together and heated for a short period of time and an organic peroxide is added. The procedure is described in co-pending U.S. application Ser. No. 299,546, filed on Oct. 20, 1972. Instead of using maleic anhydride, maleic acid or maleic halide, fumaric acid, itaconic acid or anhydride, citraconic acid or anhydride and the like acids may be used. As the olefin, monoolefins and polyolefins may be used. Polymers of such olefins as propene, butene, isobutene, hexene, octene and the like provide excellent alkenylsuccinic reactants. Monomers and oligomers of the higher olefins, such as decene, dodecene, octadecene and eicosene also provide suitable products for use in this invention. Mixtures of olefins or their polymers, when reacted with the unsaturated acid compound may produce mixed alkenylsuccinic compounds and are likewise useful. The higher molecular weight alkenylsuccinic anhydrides are preferable, especially those having from 20 to about 300 carbon atoms.

The hydroxy-substituted primary amines useful in this invention have the formula $R-NH_2$, wherein R is a hydroxy-substituted hydrocarbyl group, preferably alkyl, and contains from 1 to 30 carbon atoms and from 1 to 6 hydroxy groups. Preferably, the hydroxyl primary amine contains from 2 to about 20 carbon atoms in a branched form and one or more of the branches contains hydroxy substituents. The hydroxysubstituted alkyl primary monoamines having up to three hydroxyl groups provides satisfactory products according to this invention. Thus, R may be alkyl, cycloalkyl or aralkyl and R may also contain other substituents, such as sulfur, oxygen and the like and even additional amino groups. Alkyl and aralkyl sulfide groups and alkyl and aralkyl ether groups may be present. Polysulfide and polyethers are also useful in this invention.

These hydroxy-substituted primary amines are well known in the art and can be prepared according to conventional procedures. Examples of suitable monoamines are: 1-amino-2-hydroxyethane (or ethanolamine), 1-amino-2-hydroxypropane, 1-amino-3-hydroxypropane, 1-amino-2,3-dihydroxypropane, 1-amino-2,3,4-trihydroxybutane, 1-(hydroxymethyl)aminoethane, tris(hydroxymethyl)aminomethane, 1,1-bis(hydroxymethyl)aminoethane (or BMAM), 1-hydroxymethyl) benzyl amine and the like. The most preferred of these hydroxy-substituted primary amines is tris(hydroxymethyl) aminomethane (TMAM). It is not believed to be typical of the amine reactants as a class because it is understood to produce a novel oxazoline in the reaction product. However, the intermediate products obtained from other hydroxysubstituted primary amines are also useful herein.

The process for preparing the intermediate compounds of this invention involves reacting from 0.05 to 5 moles amine with one mole of alkenylsuccinic anhydride. The products may be imides, amides or esters of the acid reactant which products leave methylol groups or unreacted amino groups available for further reaction. The reaction mixture is heated from a temperature of about 100° C. to about 200° C. to remove a sufficient amount of water of condensation.

In forming the heterocyclic oxazoline intermediate, TMAM is reacted with the alkenylsuccinic compound at from 100° to 175° C. It is understood that the reaction of interest in this aspect of the invention proceeds as follows using TMAM as the specific reactant in a 1:1 mole ratio as an illustration:

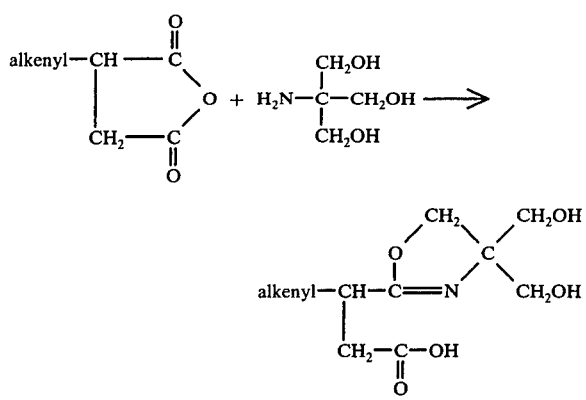

It is noted that this product, which is understood to be the predominant product in this reaction, also has functional groups which may provide reaction sites, the two methanol groups and the unused carboxyl group. Hence, further reaction by the addition of a second reactant to the reaction mixture may provide products of unique characteristics. Although the above oxazoline derivative and the other succinimide or succinic ester products provide detergent properties to lubricating oils and fuels, their derivatives, upon reaction with borates, phosphonates and aldehydes, are even more effective detergents.

The new boron-containing derivatives may be obtained by reacting the reaction product containing either the oxazoline or other components with boric acid or organoborates of the formula:

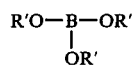

wherein each R' may individually be hydrogen or an organo group having from about 1 to 20 carbon atoms such as alkyl, cycloalkyl, aryl, aralkyl and alkaryl, including methyl, ethyl, propyl, butyl, phenyl, tolyl, benzyl and the like. Boric acid, wherein R' is hydrogen, is the most preferred.

Another class of reactants in this phase of the invention are the organophosphonates having the formula:

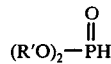

R' having the same individual identities as above. However, R' is preferably organic and not hydrogen. Suitable phosphonates include dimethylphosphonate, diethylphosphonate, dibutylphosphonate, dihexylphosphonate, diphenylphosphonate, ditolylphosphonate, and dinonylphenylphosphonate. Preparation of these phosphonates is known, such as described in U.S. Pat. No. 3,329,742.

The third reactant class useful in this invention is the aldehyde of the formula:

again, R' having the above definition. Useful aldehydes in this aspect of the invention include formaldehyde, acetaldehyde, propionaldehyde, butyraldehyde, benzaldehyde and the like.

It is not understood what the resulting structure of these boron, phosphonate or aldehyde derivatives may be. Inasmuch as the active sites of the intermediate, i.e. oxazoline or imide or ester, provide a wide variety of chemical combinations, these derivatives may be best described by the process of preparation. In any event, the invention is not limited to any particular mechanism for carrying out this phase of the invention.

The products of this invention are useful as detergents in many industrial organic fluids such as lubricating oils, mineral oils and synthetic ester or synthetic hydrocarbon oils, greases, heat exchange fluids, transmission fluids, gear oils and marine diesel oils and fuels, such as gasoline and fuel oil. Other additives may be present in these compositions, such as additional detergents, viscosity improvement agents, extreme pressure additives and oxidation stability additives. These additional additives may be ash forming or non-ash forming, including alkenylsuccinimide of alkylene polyamines, metal sulfonates, metal phenates, metal phosphorodithioates, and the like. Notably the products of this invention produce no ash and are non-metallic. These compositions may contain from 0.05% to about 20% by weight of the said additives and preferably from about 0.1 to 10%.

In the above, the boron compound may be reacted with the succinic-amine product in a ratio of from about 1 mole to about 2 moles of amine per mole of said product. The reaction temperature can range from about 50° to about 250° C, preferably from about 100° to about 200° C.

The organophosphorus reactant is reacted with the succinic amine product at from about 50° to about 250° C such that the reaction mixture contains from about 1 mole to about 2 moles of such organophosphorus compound per mole of the product.

Similarly, the aldehyde will be present in the reaction mixture to the extent of from about 1 mole to about 2 moles per mole of the succinic-amine product. The temperature can range from about 50° to about 250° C.

In all these reactions, a solvent can be used, if desired. There is no need to list them here, since one of ordinary skill in this art can easily determine those that will suit his particular reaction system and products obtained.

The following examples typify the method of preparing the products of this invention and are not deemed to be a limitation on the scope thereof. References to parts or percentages are on a weight basis unless otherwise stated. The term "mol" with regard to the polyalkenylsuccinic anhydride refers to the "mole combining" weight of the anhydride, since the anhydride may contain unreacted olefin.

EXAMPLE 1

To a suitable reactor were added 508.0 grams (0.26 mol.) of a polyisobutenylsuccinic anhydride, wherein the polyisobutenyl group contains an average of about 130 carbon atoms, and 31 grams (0.26 mol.) of TMAM and the mixture was heated to about 175° C. with stirring. Water of evaporation was removed during the reaction period. The reaction was terminated when evolution of water ceased. The reaction mixture was filtered and topped to 165° C. at reduced pressure to produce a viscous, liquid final product.

EXAMPLE 2

In a suitable reactor were mixed 500 grams (0.25 mol.) of the polyisobutenylsuccinic anhydride used in Example 1 and 60 grams (0.5 mol.) of TMAM. The mixture was heated to about 170° C. with stirring and maintained at that temperature until the evaporation of water ceased. The reaction mixture was filtered and topped as in Example 1.

EXAMPLE 3

A mixture of 2000 grams (1.0 mol.) of polyisobutenylsuccinic anhydride, prepared from a polyisobutene having about 130 carbon atoms and maleic anhydride reactant in the presence of t-butyl peroxide, and 121 grams (1.0 mol.) of TMAM was added to a suitable reactor. The mixture was heated with stirring to about 175° C. and maintained at that temperature until no further water was taken off. The mixture was cooled to 75° C. and 70 grams (1.13 mols.) of boric acid was added along with 300 grams (4.0 mols.) of butanol. The reaction mixture was then refluxed to about 225° C. over a 10 hour period. The reaction product was filtered and topped as in Example 1. Percent of boron was 0.45% of the combining weight.

EXAMPLE 4

In a suitable reactor were mixed together 300 grams (4 mols.) of normal butanol, 31 grams (0.5 mol.) of boric acid and 62 grams (0.52 mol.) of TMAM and the mixture was stirred at 100° C. for about 8 hours. To the resulting mixture was added 800 grams (0.5 mol.) of a polyisobutenylsuccinic anhydride in which the polyisobutenyl group contained an average of about 100 carbon atoms. The temperature was raised to about 200° C. over a 12-hour period. The resulting reaction mixture was filtered and topped at reduced pressure. Percent of boron is 0.48%.

EXAMPLE 5

In a suitable reactor was mixed 860 grams (0.55 mol.) of the product of Example 1, 60 grams (0.55 mol.) of dimethylphosphonate and 430 grams of a process oil diluent. The mixture was stirred at 120° to 130° F. for 4 hours then gradually heated to about 175° C. and held at this temperature for 2 hours. The reaction mixture was filtered and topped. Percent phosphorus was 1.25.

EXAMPLE 6

A mixture of 525 grams (0.26 mol.) of the polyisobutenylsuccinic anhydride, 31 grams (0.26 mol.) of TMAM, 45 grams (0.52 mol.) of formalin solution and 185 grams of a process oil diluent was gradually heated to about 200° C. over a 12-hour period with stirring. The reaction mixture was filtered and topped.

EVALUATION OF PRODUCTS

The products of this invention were evaluated in the following test: an aluminum cylinder is heated by radiant energy in an enclosed vessel. The surface temperature of the cylinder is maintained at 575° F. during 140 minutes, the duration of the test. The cylinder rotates at 2 rpm in an oil bath and the thin oil film forming on the cylinder comes into contact with a heated atmosphere (300° F.) containing air which causes oxidation of the film and oxidation deposits. The test lubricant is rated in accordance with the amount of deposits formed on the cylinder surface. On a scale of 0 to 100, the result of a 100 is a totally clean cylinder.

The base oil formulation used in this test consists of a mixture of solvent-refined mineral oils containing a total of about 3.5% by weight of an overbased magnesium organosulfonate, a zinc organodithiophosphate and a barium organodithiophosphate. The products of this invention are also present in each test formulation at a concentration of 3% by weight. As a comparison with the products of this invention, the above base formulation was also tested with 3% by weight of a commercial polyisobutenylsuccinimide of tetraethylenepentamine, the polyisobutenyl group having a molecular weight of about 900.

The following results were obtained:

| Additive | Rating |
| --- | --- |
| None (base fluid alone) | 62 |
| Commercial succinimide | 74 |
| Example 1 | 84 |
| Example 2 | 82 |
| Example 3 | 85 |
| Example 4 | 87 |
| Example 5 | 83 |
| Example 6 | 88 |

Having described my invention in both broad and narrow terms, it is clear that the invention is susceptible to both broad and narrow modifications and I do not wish to be limited to such interpretations other than as claimed in the following claims.

I claim:

1. A product prepared by reacting, at a temperature of from about 100° to about 200° C., one mole of alkenylsuccinic acid, anhydride or acyl halide with from 0.05 to 5 moles of a hydroxylated primary amine selected from the group consisting of 1-amino-2-hydroxypropane, 1-amino-3-hydroxypropane, 1-amino-2,3-dihydroxypropane, 1-amino-2,3,4-trihydroxybutane, 1-(hydroxymethyl)aminoethane, tris(hydroxymethyl)-aminomethane, 1,1-bis (hydroxymethyl)aminoethane and 1-(hydroxymethyl)benzylamine and reacting the resulting product with a reactant selected from the group consisting of (1) from about 1 to about 2 moles per mole of said product of a boron compound of the formula

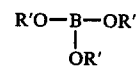

in which each R' is individually selected from the group consisting of hydrogen and a $C_1$–$C_{20}$ alkyl, aralkyl or aralkyl group, (2) from about 1 mole to about 2 moles per mole of said product of an organophosphonate of the formula

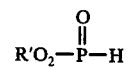

in which R' is individually selected from the group consisting of hydrogen and a $C_1$–$C_{20}$ alkyl, arayl, aralkyl or alkaryl group (3) or from about 1 mole to about 2 moles per mole of said product of an aldehyde of the formula

in which R' is selected from the group consisting of hydrogen and a $C_1$-$C_{20}$ alkyl, aryl, aralkyl or alkaryl, the reaction of the boron, phosphonate or aldehyde with said product taking place at from about 50° to about 250° C.

2. The product of claim 1 wherein the amine is tris(-hydroxymethyl)aminomethane.

3. The product of claim 1 wherein the reactant is selected from the group consisting of boric acid, dimethylphosphonate and formaldehyde.

4. The product of claim 3 wherein the reactant is boric acid.

5. The product of claim 3 wherein the reactant is dimethyl phosphonate.

6. The product of claim 3 wherein the reactant is formaldehyde.

7. An organic fluid composition comprising a major proportion of a mineral lubricating oil, a synthetic lubricating oil, a grease prepared from these or a normally liquid hydrocarbon fuel and a detergent amount of a product prepared by reacting one mole of alkenylsuccinic acid, anhydride or acyl halide with from 0.05 to 5 moles of a hydroxylated primary amine selected from the group consisting of 1-amino-2-hydroxypropane, 1-amine-3-hydroxypropane, 1-amine-2,3-dihydroxypropane, 1-amino-2,3,4-trihydroxybutane, 1-(hydroxymethyl)aminoethane, tris(hydroxymethyl)-aminomethane, 1,1-bis(hydroxymethyl)aminoethane and 1-(hydroxymethyl) benzylamine and reacting the resulting product with a reactant selected from the group consisting of (1) from about 1 to about 2 moles per mole of said product of a boron compound of the formula

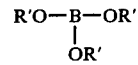

in which each R' is individually selected from the group consisting of hydrogen and a $C_1$-$C_{20}$ alkyl, aralkyl or aralkyl group, (2) from about 1 mole to about 2 mole of said product of an organophosphonate of the formula

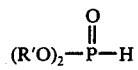

in which R' is individually selected from the group consisting of hydrogen and a $C_1$-$C_{20}$ alkyl, arayl, aralkyl or alkaryl group or (3) from about 1 mole to about 2 moles per mole of said product of an aldehyde of the formula

in which R' is selected from the group consisting of hydrogen and a $C_1$-$C_{20}$ alkyl, aryl, aralkyl or alkaryl, the reaction of the boron, phosphonate or aldehyde with said product taking place at from about 50° to about 250° C.

8. The composition of claim 7 wherein the amine is tris(hydroxymethyl)aminomethane.

9. The composition of claim 7 wherein the reactant is selected from the group consisting of boric acid, dimethyl phosphonate and formaldehyde.

10. The composition of claim 9 wherein the reactant is boric acid.

11. The composition of claim 9 wherein the reactant is dimethyl phosphonate.

12. The composition of claim 9 wherein the reactant is formaldehyde.

* * * * *

UNITED STATES PATENT AND TRADEMARK OFFICE
CERTIFICATE OF CORRECTION

PATENT NO. : 4,097,389
DATED : June 27, 1978
INVENTOR(S) : HARRY J. ANDRESS, JR.

It is certified that error appears in the above-identified patent and that said Letters Patent are hereby corrected as shown below:

Column 6, Claim 1 (second formula)

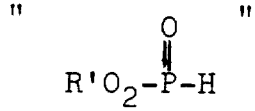

should read

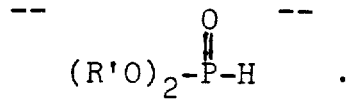

Column 8, Claim 7 (col. 2-line 8) "mole" (second occurrence) should read --moles--.

Signed and Sealed this

Nineteenth Day of December 1978

[SEAL]

Attest:

RUTH C. MASON
Attesting Officer

DONALD W. BANNER
Commissioner of Patents and Trademarks